United States Patent [19]

Yamamura

[11] Patent Number: 4,732,739
[45] Date of Patent: Mar. 22, 1988

[54] AMALGAM PREPARING CHAMBER AND MERCURY-CAPTURING DEVICE

[75] Inventor: Yoshinobu Yamamura, Kawasaki, Japan

[73] Assignee: G-C Dental Industrial Corp., Tokyo, Japan

[21] Appl. No.: 852,364

[22] Filed: Apr. 15, 1986

[30] Foreign Application Priority Data

Jun. 4, 1985 [JP] Japan ............................. 60-83333[U]

[51] Int. Cl.⁴ ........................ B01D 50/00; A61C 5/06
[52] U.S. Cl. .................................... 422/170; 422/193; 366/602
[58] Field of Search ............... 422/129, 149, 170, 193; 366/602

[56] References Cited

FOREIGN PATENT DOCUMENTS 2810678  9/1978  Fed. Rep. of Germany ...... 366/602

*Primary Examiner*—David L. Lacey
*Attorney, Agent, or Firm*—Oblon, Fisher, Spivak, McClelland & Maier

[57] ABSTRACT

An amalgam-preparing chamber and mercury-capturing device therefor, which includes an amalgam-preparing chamber which is positioned on top of a mercury-capturing device, and wherein:

(a) the amalgam-preparing chamber includes a space enclosed by a wall having a plate base at the lower end of the space, and wherein the wall has a transparent section, the base having a plurality of small openings into the mercury-capturing device; and an amalgam-preparing device in the enclosed space, and whereby the enclosed space is exposed to view by the transparent section in the wall, and further wherein the chamber has an openable door therefore; and wherein:

(b) the mercury-capturing device includes:
  (i) an upper closed separation chamber in flow communication with the openings in the base, and
  (ii) a lower mercury vapor treatment chamber, wherein the upper and lower chambers are separated by an inclining partition which extends downwardly into a mercury reservoir groove with a discharge cock at the lower edge thereof, and wherein a vertically extended mercury vapor suction pipe extends through the inclining partition and has a downward suction inlet at the upper portion of the pipe in the upper closed separation chamber above the mercury reservoir groove, and wherein the lower portion of the pipe extends through the inclining chamber partition into a mercury-capturing device which is connected in sequence to a check trap, neutralization device and a pump.

10 Claims, 3 Drawing Figures

AMALGAM PREPARING CHAMBER AND MERCURY-CAPTURING DEVICE

FIELD OF THE INVENTION

The present invention relates to an apparatus for the prevention of mercury pollution, so as to prevent environmental pollution caused by scattered mercury particles, amalgam particles, mercury vapor, etc., that are produced during amalgam mixing.

BACKGROUND OF THE INVENTION

Amalgams or alloys of metal powders composed mainly of silver and mercury, have long been used as dental filling materials. However, various dental filling materials have recently been studied and developed for the purpose of preventing such environmental pollution. Due to the fact that such amalgams have high strength, assure easy manipulation during treatments, and are harmless in the mouth, their usefulness is being reconsidered. However, mercury is essentially a harmful substance to which severe environmental standards are applied. Due to its unique properties, mercury metal poses a severe pollution threat. To prevent such pollution, it is preferred that scattered mercury particles, etc. be contained in a specific place or a closed system for collection. Following such an idea, a mercury pollution-preventing apparatus has been developed and used, wherein the preparation of amalgams can be carried out in such a manner that environmental pollution due to mercury is reduced. For instance, an apparatus is known which contains an amalgam-preparing chamber having therein a space defined on a plate base having a number of small openings by the walls, wherein one of them is at least transparent and includes a openable door, the space being designed to receive an amalgam-preparing device, a funnel attached at the top to the lower end of such chamber in a closed state and without any gap therebetween, a vertically movable water tank into which a funnel pipe extending from the central bottom of said funnel is inserted, a mercury vapor-capturing bin filled with an absorbent composed of wool, etc. or activated charcoal, and an electrically driven pump.

With the aforesaid apparatus, however, it is very difficult to determine when the activated charcoal or absorbent is used up. Misjudgment of replacement time leads to environmental pollution due to mercury. On the contrary, frequent replacement results in waste of material and hence a rise in the processing cost. In addition, the mercury vapor-capturing power is rather low. Since all the scattered mercury, amalgam pieces and mercury vapor generated in the amalgam-preparing chamber are allowed to pass through the fine funnel pipe, there is an increase in the flow rate of nongaseous mercury such as fine mercury particles or amalgam particles. Hence, the nongaseous mercury in the gas stream is captured in water by passing it through the water tank, but it is, in most cases, impossible to prevent a portion of these fine particles from reaching the bin. As a result, the service life of the absorbent or activated charcoal is not only reduced, but the amount of nongaseous mercury captured in the bin such as fine mercury particles varies from time to time and from place to place. This results in further misjudgment of replacement time.

SUMMARY OF THE INVENTION

A main object of the present invention is to provide an apparatus for preventing mercury pollution which is free from the problems of the prior art, and is designed to be particularly useful in the dental field.

The apparatus of the present invention entails an amalgam-preparing chamber including a space defined by a wall with a plate base at the lower end having a number of small openings, and one of them is at least partly transparent and includes an openable door, with an amalgam-preparing device located in such space, and a mercury-capturing means which is attached at the top to the lower end of the chamber in a closed state and without any gap therebetween, and which captures an amount of mercury vapor which is generated in said chamber and passes through the small openings in the plate base, and which is characterized by having an inclining plate that extends downwardly from the upper portion of one wall of such means to the opposite wall to divide the interior of such means into an upper closed separation chamber and a lower mercury vapor treatment chamber, and which is provided at its lower end with a mercury reservoir groove having a discharge cock, wherein the treatment chamber includes a mercury vapor-capturing vessel charged therein with a mercury vapor-capturing liquid containing a solution containing compounds of tri- or higher-valent manganese, a check trap, a reducing agent liquid-filled neutralization vessel and a suction pump. A mercury vapor suction pipe extends through an inclining plate and includes an upper downward inlet port and wherein the piping is arranged in such a manner that a gas stream drawn from the port under the action of the pump is supplied from the lower end of the pipe to the pump successively through the capturing liquid, the trap and the reducing agent liquid, whereby mercury vapor can be captured, while observing the captured liquid in the vessel from the side of the means.

BRIEF DESCRIPTION OF THE DRAWING

The objects and features of the present invention will become apparent from the following detailed description with reference to the accompanying drawings, which are given for the purpose of illustration alone, and in which.

DETAILED DESCRIPTION OF THE INVENTION

Figure 1:
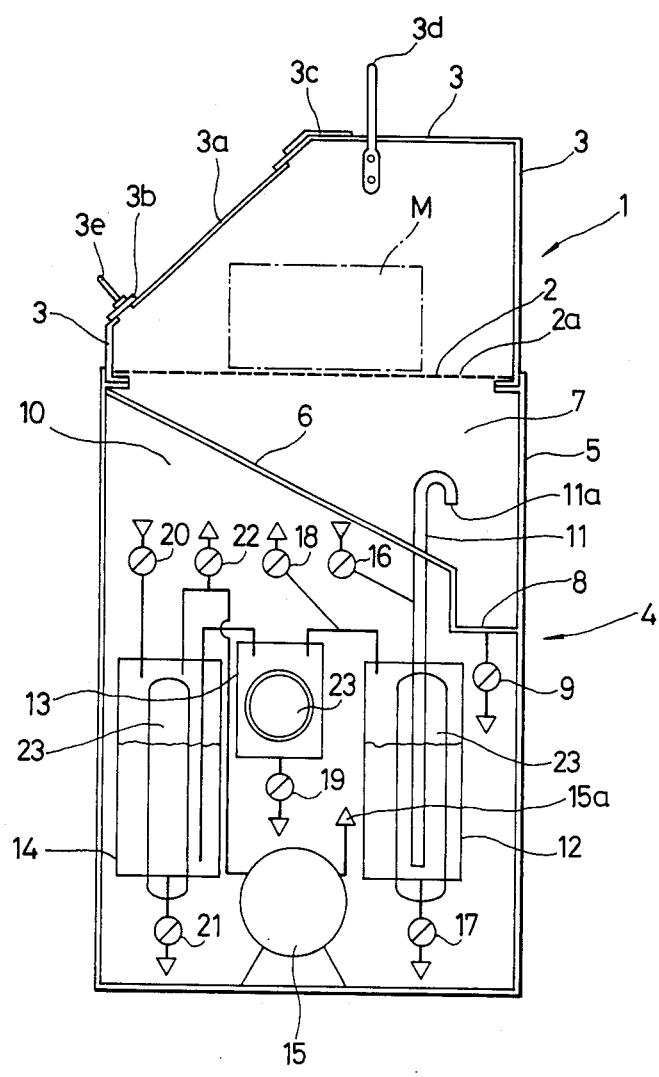
FIG. 1 is a side view showing the interior of the apparatus according to the present invention.
Figure 2:
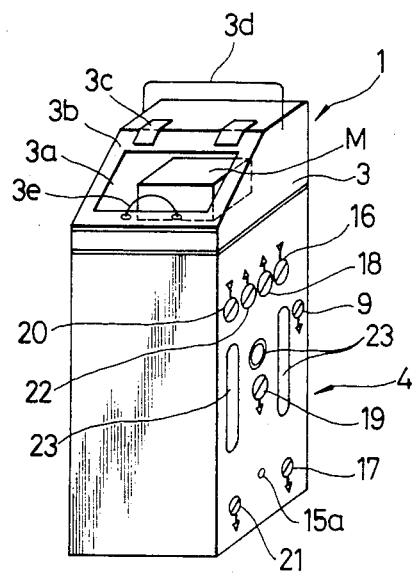
FIG. 2 is a perspective view showing the exterior of the apparatus of FIG. 1.

Referring to the drawings, an amalgam-preparing chamber, generally shown at 1, has therein a space defined by a wall 3 on a plate base 2 of, e.g., stainless steel, having a number of small openings 2a, said space being sufficiently capable of accommodating an amalgam-preparing device M. As shown in FIG. 2, the wall 3 is at least partly formed of a transparent portion 3a so that the device M received in the chamber 1 is exposed to open view, and includes an openable door 3b which can be opened or closed by means of a hinge 3c. In the illustrated embodiment, the transparent portion 3a is located in the openable door 3b. It is understood, however, that, in addition thereto or instead thereof, it may be located at other portions. Preferably, the door 3 is provided with an associated handle 3d and a doorknob 3e. As illustrated in FIG. 1, the plate base 2 may be incorporated into the lower end portion of the wall 3 defining the chamber 1. Alternatively, it may be separate from the wall 3 to define the chamber 1 therewith, when it is positioned on the top of a mercury-capturing means which will be described below. The amalgam-preparing chamber 1 is mounted at its lower end edge upon the mercury capturing means without making any gap therebetween. When the openable door 3b is closed, the chamber 1 is isolated from the outside in a closed state. Reference numeral 4 stands for the mercury capturing means, the interior of which is divided into an upper closed separation chamber 7 and a lower mercury vapor treatment chamber 10 by an inclining partition or plate 6 downwardly extending from the upper portion of one side wall to the opposite side wall, as illustrated in FIG. 1. The inclining partition 6 is then provided with a mercury reservoir groove 8 at the lower edge, which has a mercury discharge cock 9 provided at the bottom, as illustrated in FIG. 1. A mercury vapor suction pipe 11 extends through the inclining partition 6, and includes at its upper portion a downward suction inlet 11a within the chamber 7, as illustrated in FIG. 1. There mercury vapor treatment chamber 10 includes a mercury vapor capturing vessel 12, a check trap 13, a neutralization vessel 14 and a suction pump 15, as shown in FIG. 1. The vessel 12 is charged with a mercury vapor capturing liquid comprising an acidic solution containing compounds of tri- or higher-valent manganese such as permanganates, manganates, manganic sulfate, etc. Referring to the solution composition, it may have a potassium permanganate composition of 0.01 mol/l or higher and a sulfuric acid concentration of 0.3N or higher. For instance, the amounts of potassium permanganate and sulphuric acid may be 0.5% by weight and 5% by weight, respectively. Using such a mercury vapor capturing liquid as progress of the mercury vapor treatment can be monitored by, discoloration, formation of brown precipitates, and a decrease in the amount of precipitates. Thus, this solution differs in composition and appearance from to time to time.

The neutralization vessel 14 is charged with reducing agent solution. Preferably, a weak reducing agent such as methanol should be used. For instance, use may be made of a 3% by weight aqueous methanol solution. As will be seen from FIG. 1, piping is arranged in such a manner that a vapor stream sucked from the downward inlet 11a under the suction force of the pump 15 passes from the lower end of the pipe 11 to the pump 15 successively through the vapor capturing liquid (filled in the vessel 12), the check trap 13 and the reducing agent liquid (filled in the neutralization vessel 14), and is discharged from a discharge port 15a thereof. For filling or discharging of the mercury vapor capturing liquid or the reducing agent liquid, an inlet cock 16, an outlet cock 17, an exhaust cock 18, an outlet cock 19, an inlet cock 20, an outlet cock 21 and an exhaust cock 22 are respectively attached to the mercury suction pipe 11, the bottom of the mercury vapor capturing vessel 12, a pipe for connecting the vessel 12 with the check trap 13, the bottom of the check trap 13, the neutralization vessel 14, the bottom of the vessel 14 and a pipe for connecting the vessel 14 with the pump 15.

Reference will now be made to the form and structure of the mercury vapor capturing means.

It is necessary that the separation chamber 7 be kept airtight therearound. However, it is not always necessary to surround the mercury vapor treatment chamber 10 therearound in an air-tight manner with a wall, since mercury vapor is treated in a closed system. No limitation is imposed upon the form and structure of the wall defining capturing means 4, as long as the mercury vapor capturing liquid within the vessel 12 can be observed from each side, and mercury can be captured.

For instance, it is possible to manipulate the cocks and observe the interior of each of the vessels 12 and 14 at one's disposal in the absence of any wall. Considering appearance and safety, however, it is preferred that the present mercury capturing apparatus is as a whole surrounded with walls, one of which is provided with the cocks 9, 16, 17, 18, 19, 20, 21 and 22, the exhaust port 15a for the pump 15, and viewing windows 23 for the vessels 12 and 14.

Figure 3:
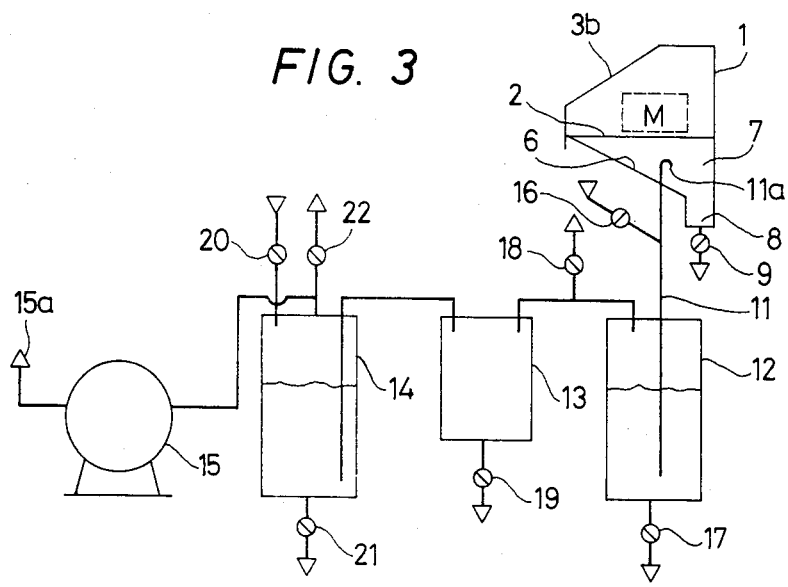
FIG. 3 is a flow sheet showing the action of the apparatus of FIG. 1 in use.

In using the apparatus according to the present invention, the required materials such as mercury, silver, etc. are first charged into the amalgam-preparing device M, which is, in turn, set in the amalgam-preparing chamber 1, as illustrated in FIG. 3. The suction pump 15 is actuated to start draining a gas stream and putting the device M into operation, whereby the chamber 1 is kept air-tight. A portion of mercury leaking or vaporizing from the device M passes downwardly through the small openings 2a in the plate base 2. However, so low is the flow rate of gas in the separation chamber 7 that nongaseous mercury such as mercury droplets or amalgam particles is stored in the mercury reservoir groove 8 along the inclining plate 6. Since the inlet portion 11a in the suction pipe 11 directs downwardly, it receives only a gas stream containing mercury. Thus, there is no fear that nongaseous mercury may possibly be drawn into the suction pipe 11. Preferably, the groove 8 is pre-charged with an amount of water or oil so as to prevent evaporation of mercury. A mercury vapor entering the pipe 11 is guided from its lower end into the mercury vapor-capturing liquid (hereinafter referred to as the capturing liquid) in the vessel 12, in which mercury is captured in the form of mercury salts. The action of the capturing liquid comtaining an acidic solution containing compounds of tri- or higher-valent manganese is disclosed in Japanese Patent Publication No. 42-22444. According to the teachings of that publication, when the capturing liquid is used in a state where it is still not in contact with mercury vapor, slightly soluble manganese compounds are formed as brown precipitates. As mercury vapor in the gas stream starts acting upon the compounds slightly dissolved in the capturing liquid, mercury is captured in the capturing liquid in the form of mercury salts. With the progress of this reaction, the brown precipitates are dissolved little by little in the capturing liquid. As the precipitates disappear completely, its mercury-capturing power disappears. Referring to an example of the mercury-capturing power at the time when the brown precipitates are present in the capturing liquid used with the apparatus of the present invention, the concentrations of mercury in the gases discharged out of the pump 15 were 0.5 and 2 $\mu g/m^3$, when the original concentrations of mercury in the chamber 1 were 210, 170 and 150 $\mu g/m^3$.

The gas stream, from which mercury vapor has been removed by passing the stream through the mercury vapor-capturing vessel 12, is guided into the reducing agent liquid in the neutralization chamber 14 via the check trap 13. In that reducing agent liquid, a minute amount of oxidizing compounds, which may possibly be present in the gas stream, is removed so as to prevent damage of the pump 15 or air pollution. The gas stream is then discharged out of the port 15a in the pump 15. Upon the completion of amalgam-preparation, the device M is removed, and the cock 9 is opened for the removal of nongaseous mercury from the groove 8. As already mentioned, the capturing liquid maintains its mercury-capturing power, while the brown precipitates do not disappear. In consequence, the most effective time for replacement is just before the brown precipitates disappear, and is easily determined. The reducing agent liquid may be used over a considerably extended period, and may be replaced at a suitable time. Preferably, the replacement of the reducing agent liquid is effected, when it turns to dark brown, by way of an oxidation-reduction indicator such as diphenylamine-4-sulfonic acid sodium, added thereto in a concentration of 20 to 30 ppm.

The replacement of each liquid will be explained with reference to FIG. 3. A fresh capturing liquid is supplied by opening the cock 16, after the used-up capturing liquid has been removed by opening the exhaust cock 18 and the discharge cock 17. A fresh reducing agent liquid is fed by opening the inlet cock 20, after the used-up liquid has been removed by opening the exhaust cock 22 and the discharge cock 21. The thus removed nongaseous mercury, capturing liquid and reducing agent liquid should be properly handled. Especially, the mercury and the capturing liquid should be controlled and processed according to the prescribed manner so as to prevent environmental pollution.

I claim:

1. An amalgam-preparing chamber and mercury-capturing device therefor, which comprises an amalgam-preparing chamber which is positioned on top of a mercury-capturing means, and wherein:
   (a) said amalgam-preparing chamber, comprises a space enclosed by a wall having a plate base at the lower end of said space, and wherein the wall has a transparent section, said base having a plurality of small openings into said mercury-capturing means; and an amalgam-preparing device in said enclosed space, and whereby said enclosed space is exposed to view by said transparent section in said wall, and further wherein said chamber has an openable door therefore; and wherein:
   (b) said mercury-capturing means comprises:
      (i) an upper closed separation chamber in flow communication with the openings in said base, and
      (ii) a lower mercury vapor treatment chamber, wherein the upper and lower chambers are separated by an inclining partition which extends downwardly into a mercury reservoir groove with a discharge cock at the lower edge thereof, and wherein a vertically extended mercury vapor suction pipe extends through the inclining partition and has a downward suction inlet at the upper portion of the pipe in the upper closed separation chamber above the mercury reservoir groove, and wherein the lower portion of the pipe extends through the inclining chamber partition into a mercury-vapor capturing means which is connected in sequence to a check trap, neutralization means and a pumping means.

2. The apparatus of claim 1, wherein said mercury vapor-capturing means contains a mercury vapor-capturing liquid comprising a solution containing a manganese compound having a manganese valence of three or more.

3. The apparatus of claim 2, wherein said mercury vapor-capturing liquid comprises an acidic solution.

4. The apparatus of claim 3, wherein said manganese compounds are manganates, permanganates or manganic sulfate.

5. The apparatus of claim 4, wherein said liquid comprises a solution of potassium permanganate at a concentration of 0.01 mol/l, or more, and sulfuric acid at a concentration of 0.3N or higher.

6. The apparatus of claim 1, wherein said mercury-vapor suction pipe extending through said inclining partition is arranged in such a manner so as to enable a gas stream to be drawn from the downward suction inlet by said pumping means successively through the mercury vapor-capturing means, said trap, and said neutralization vessel.

7. The apparatus of claim 1, wherein said neutralization means contains a liquid reducing agent.

8. The apparatus of claim 7, wherein said liquid reducing agent is a weak reducing agent.

9. The apparatus of claim 8, wherein said liquid reducing agent is a 3% by weight aqueous solution of methanol.

10. The apparatus of claim 1, wherein said mercury reservoir groove is charged with an amount of water or oil sufficient to prevent evaporation of mercury therefrom.

* * * * *